United States Patent [19]

Leston

[11] 4,267,390

[45] May 12, 1981

[54] PROCESS FOR OBTAINING PARA-CRESOL AND META-CRESOL FROM A MIXTURE OF METHYLATED AND ETHYLATED PHENOLS CHARACTERIZED BY SELECTIVE COMPLEXATION WITH CALCIUM BROMIDE AND SODIUM ACETATE

[75] Inventor: Gerd Leston, Pittsburgh, Pa.

[73] Assignee: Koppers Company, Inc., Pittsburgh, Pa.

[21] Appl. No.: 53,195

[22] Filed: Jun. 29, 1979

[51] Int. Cl.³ .................... C07C 37/68; C07C 37/74
[52] U.S. Cl. .................................. 568/751; 568/750
[58] Field of Search ....................... 568/751, 750, 752

[56] References Cited

U.S. PATENT DOCUMENTS

| 1,980,384 | 11/1934 | Comte | 568/751 |
|---|---|---|---|
| 2,042,331 | 5/1936 | Carswell | 568/751 |
| 2,366,538 | 2/1945 | Luten | 568/751 |
| 2,835,714 | 5/1958 | Nixon et al. | 568/751 |

FOREIGN PATENT DOCUMENTS 51-98228  9/1976  Japan .................................. 568/751

OTHER PUBLICATIONS

Sharpless, et al. "Jour. Organic Chemistry" vol. 40, #9 (1975), Rapid Separation of Organic Complexes by Formation of Metal Complexes.

*Primary Examiner*—Werren B. Lone
*Attorney, Agent, or Firm*—J. Timothy Keane; Oscar B. Brumback

[57] ABSTRACT

A process is disclosed for the stepwise separation of para-cresol and meta-cresol from a mixture of methylated and ethylated phenols. The para-cresol forms a complex with a dehydrated or anhydrous inorganic halide salt selected from the group consisting of calcium bromide, lithium bromide, manganese bromide and magnesium chloride. The meta-cresol isomer is separated from the mixture by formation of a complex with sodium acetate. Where the anhydrous or dehydrated inorganic halide salt is added firstly to the mixture of methylated and ethylated phenols including para-cresol and meta-cresol, the halide salt is provided in an amount to give a mole ratio of the halide salt to para-cresol in the mixture in the range of about 0.5 to one to about 1.5 to one. The para-cresol complexes with the halide salt and the complex is then removed from the mixture. The para-cresol-salt complex is thereafter decomposed to recover the para-cresol. The mixture of methylated and ethylated phenols including meta-cresol from which the para-cresol has been removed has added to it sodium acetate in an amount to give a mole ratio of sodium acetate to meta-cresol in the mixture in the range of about 0.5 to one to about 5 to one. The meta-cresol sodium acetate complex is then separated from the mixture of methylated and ethylated phenols and thereafter the complex is decomposed to produce a high purity meta-cresol. It is a feature of the invention that either of the complexing steps may be performed first; that is, either of the anhydrous halide salt or the sodium acetate may be added to the mixture, followed thereafter by addition of the other complexing agent.

29 Claims, 1 Drawing Figure

PROCESS FOR OBTAINING PARA-CRESOL AND META-CRESOL FROM A MIXTURE OF METHYLATED AND ETHYLATED PHENOLS CHARACTERIZED BY SELECTIVE COMPLEXATION WITH CALCIUM BROMIDE AND SODIUM ACETATE

CROSS-REFERENCE TO RELATED APPLICATIONS

This application is related to applications entitled "Process for Separating Para-Cresol from a Mixture of Methylated and Ethylated Phenols," Ser. No. 53,438, "Process for Obtaining Para-Cresol and Meta-Cresol from a Mixture of Methylated and Ethylated Phenols Containing Meta- and Para-Cresol," Ser. No. 53,532, and "Process for Obtaining Para-Cresol and Meta-Cresol from a Mixture of Methylated and Ethylated Phenols Characterized by Urea Clathration of Meta-Cresol," Ser. No. 53,531, all of Gerd Leston, filed on June 29, 1979, which applications are hereby incorporated by reference.

BACKGROUND OF THE INVENTION

The present invention relates to a process for separating para-cresol and meta-cresol from a mixture of methylated and ethylated phenols. More particularly, the process is directed to obtaining separately high purity para-cresol and meta-cresol isomers from a mixture of methylated and ethylated phenols.

Mixtures of methylated and ethylated phenolic compounds may be derived from coal as products of coal carbonization, as the middle oil from the hydrogenation of coal, from the liquefaction of coal, or from petroleum as alkaline extracts of cracked petroleum distillate. Some of the methylated and ethylated phenols in a mixture derived from these sources have similar physical properties. These similarities in properties make it difficult to separate some of the phenolic compounds from each other. Para-cresol and meta-cresol are compounds that are usually present in mixtures of methylated and ethylated phenols, and they are difficult to separate from the other methylated and ethylated phenols and from each other. For example, para-cresol is difficult to separate from meta-cresol since both compounds have similar boiling points, namely, 201.8° C. and 202.8° C., respectively. The similarity of boiling points of these two compounds precludes their separation by simple distillation and also makes fractional distillation a complicated procedure.

There are several known methods for separating para-cresol and meta-cresol isomers from a mixture containing the isomers, such as a commercial mixture having 40-65 percent of meta-cresol. These methods include treatment of a mixture containing meta- and para-cresol isomers with complexing agents such as urea, sodium acetate, oxalic acid or the like and separation of the meta- or para-cresol isomers in an adduct form. Other methods include the formation of a solid complex between a reagent and one cresol isomer. The reagents used include ortho-toluidine, oxalic acid and hexamethylene-tetramine. Still other methods for separating meta- and para-cresol isomers involve azeotropic distillation with benzyl alcohol, or selective solvent extraction with methanol-ligroin, or hydrolysis of the sulfonic acid of meta- or para-cresol, or dibutylation followed by distillation and debutylation. Another recently suggested method for separating meta-cresol and para-cresol isomers takes advantage of the different melting points of the compounds and involves subjecting the meta- and para-cresol isomer mixture to crystallization at pressures of not less than about 300 atmospheres. Only a few of the foregoing methods of separation have any commercial potentialities, the process usually employed being the butylation method. A more efficient method is thus desired to obtain high purity para-cresol and high purity meta-cresol from mixtures of methylated and ethylated phenols containing compounds such as ortho-ethyl-phenol, xylenol and other methylated and ethylated phenols having similar boiling points to para-cresol and meta-cresol.

An article entitled "Rapid Separation of Organic Mixtures by Formation of Metal Complexes", Journal Organic Chemistry, Volume 40, No. 9, 1975, Sharpless, Chong and Scott, describes a convenient and efficient technique for resolving alcohol mixtures. The technique involves preferential complexing of an alcohol by calcium chloride or manganese chloride, examples of useful alcohols being cis- and trans-4-tert-butylcyclohexanol, geraniol, and cyclohexanol. The article further notes that other alcohols, such as large and hindered alcohols, form complexes very slowly, and that the speed of complex formation can be increased by using a small amount of a lower aliphatic alcohol as a catalyst for complexing.

SUMMARY OF THE INVENTION

The present invention provides a process which includes a novel combination of cresol isomer separation steps. The process comprises a two-step separation of para-cresol and meta-cresol from a mixture of methylated and ethylated phenols by complexation of each of the isomers with different components. It is an advantage of the present process that the isomer complexation reactions may be accomplished in any order, that is, either of the para-cresol or meta-cresol isomers may be separated from the mixture, followed thereafter by separation of the remaining isomer. The process comprises the steps of (a) for separation of para-cresol isomer: adding to a mixture of methylated and ethylated phenols containing para-cresol and meta-cresol isomers and methylated and ethylated phenols having similar boiling points to para-cresol and meta-cresol, one or more anhydrous or dehydrated inorganic halide salts selected from the group consisting of calcium bromide, lithium bromide, manganese bromide and magnesium chloride in an amount sufficient to produce a complex between predominantly para-cresol and the halide salt, whereby the para-cresol-salt complex may be separated from the mixture, and then decomposed to produce predominantly para-cresol; and (b) for separation of the meta-cresol isomer: adding to the mixture of methylated and ethylated phenols an amount of sodium acetate sufficient to produce predominantly meta-cresol-sodium acetate complex, whereby the meta-cresol-sodium acetate complex may be separated from the mixture, and then decomposed to produce predominantly a high purity meta-cresol. The amount of anhydrous or dehydrated inorganic halide salt added to the mixture of methylated and ethylated phenols to produce a para-cresol salt complex is added in the amount to give a mole ratio of salt to para-cresol in the mixture in the range of about 0.5 to one to 1.5 to one. This addition of the halide salt is preferably conducted in the presence of a non-aqueous solvent. The addition of the sodium acetate to the mixture of methylated and ethylated phenols is preferably performed with an amount of sodium acetate to give a mole ratio of sodium acetate to meta-cresol in the mixture in the range of about 0.5 to one to about 5 to one. This addition is also preferably performed in the presence of a non-aqueous solvent. The order of separation of the isomers may be step (a) followed by step (b) or may be step (b) followed by step (a).

In the process of the present invention, important variables include the halide salt to para-cresol mole ratio and, to a lesser extent, the variables of para-cresol concentration in the mixture of methylated and ethylated phenols, the solvent used and the temperature of complexing. The halide salt to para-cresol mole ratio is generally in the range of about 0.5 to one to about 1.5 to one. The para-cresol concentration in the mixture of methylated and ethylated phenols can be any concentration, but generally is at least that concentration that can be purified or separated economically. When the amount of para-cresol in the mixture is low, e.g., on the order of 10 percent, the preferential complexing of the para-cresol can be enhanced by the use of higher temperatures in the order generally of about 70° C. to 130° C. The mixture of methylated and ethylated phenols contains, in addition to para-cresol and meta-cresol, other methylated and ethylated phenols having similar boiling points with the para-cresol. The solvent used should be a non-aqueous solvent, since water will react with the anhydrous inorganic halide salt to form one or more hydrates. Generally, the non-aqueous solvent should not, itself, complex with the halide salt or at least not more readily than the para-cresol. The addition of the halide salt to the mixture of methylated and ethylated phenols can be initially with or without the use of the solvent, but once the halide salt is added to the mixture, a solvent should then be employed to facilitate the mixing of the halide salt and the mixture. Generally the temperature at which complexing occurs ranges from ambient temperatures to a temperature of about 130° C., depending upon the concentration of para-cresol in the mixture of methylated and ethylated phenols. If the complex formation is not initiated at higher temperatures, the temperature can be lowered to initiate complex formation, and then raised to a higher temperature. If the para-cresol-salt complex formation is slow, an initiator, such as a lower aliphatic alcohol or a previously formed complex of the para-cresol and halide salt, can be used to initiate the complexing reaction. Once the para-cresol-salt complex is formed, it may be separated from the mixture by any method known to those skilled in the art for separating solid complexes from liquids. Once separated, the para-cresol-salt complex can be decomposed by thermal decomposition at atmospheric pressure, or by distillation at reduced pressure, or by treatment with water, or by treatment with alcohol. When the complex is decomposed, the high purity para-cresol is recovered and the anhydrous inorganic halide salt can be recycled for further complex formation with para-cresol, if the decomposition occurs thermally or by distillation.

In the meta-cresol separation stage, wherein the meta-cresol isomer is separated from the mixture of methylated and ethylated phenols, the important variables are the concentration of the meta-cresol in the mixture, the temperature of complexing, and the concentration of sodium acetate used. Generally, the amount of sodium acetate utilized is within a mole ratio of sodium acetate to meta-cresol in the range of about 0.5 to one to about 5 to one; preferably the mole ratio is in the range of about 1 to one to about 3 to one. The temperature of complexing of the meta-cresol and the sodium acetate may be in the range of about 0° C. to about 75° C. at atmospheric pressure. The type of solvent used and the manner of separation of the complex from the mixture of methylated and ethylated phenols and the manner of decomposing the meta-cresol-sodium acetate complex and the recycling of the sodium acetate are similar to those used in the formation of the para-cresol-salt complex.

When the para-cresol-salt complex and meta-cresol-sodium acetate complex are separated from the mixture of methylated and ethylated phenols, it is best to dry the complexes and recycle any non-aqueous solvent obtained in the drying process. The non-aqueous solvent can be recycled to the complex-forming step.

DETAILED DESCRIPTION OF THE INVENTION

In the process of the present invention, para-cresol and meta-cresol can be obtained in high purity form from a mixture of methylated and ethylated phenols having similar boiling points to the para-cresol and meta-cresol isomers. Non-limiting examples of the methylated and ethylated phenolic compounds of the mixture include ortho-cresol, ortho-ethylphenol, thymol, xylenol and trimethylphenols. It is preferred that the mixture contain substantial quantities of para-cresol and meta-cresol; a suitable mixture is a commercial mixture of meta- and para-cresol isomers which contains from 40–65 percent of the meta-cresol isomer, the remaining being the para-cresol isomer. Also, the preferred methylated and ethylated phenolic compounds are those methylated phenols that do not form complexes with the anhydrous inorganic halide salts of calcium bromide, lithium bromide, manganese bromide or magnesium chloride, or that are not thermodynamically favored over the para-cresol-salt complex, or that form complexes at a slower rate than para-cresol and meta-cresol.

The process of the present invention is based on the discovery that certain anhydrous or dehydrated inorganic halide salts, when used in a certain mole ratio to para-cresol in the mixture of methylated and ethylated phenols, preferentially complex with the para-cresol. The described useful anhydrous halide salts, especially calcium bromide, also tend to form complexes with the meta-cresol isomer. It is believed, however, that the formation of the para-cresol-salt complex is thermodynamically controlled while the formation of the meta-cresol-calcium bromide complex is kinetically controlled. Thus, while the rate of the meta-cresol-calcium bromide complexation may be higher than that of the para-cresol-calcium bromide complexation at certain high concentrations of the meta isomer, formation of the para-cresol-calcium bromide complex will ultimately prevail because the para-cresol complex is more thermodynamically stable than the meta isomer complex. It is a feature of the present process that when separation of the meta isomer is undertaken firstly, complexation of the meta isomer with sodium acetate occurs preferentially and selectively over the para isomer.

The amount of para-cresol in the mixture of methylated and ethylated phenols, and preferably in the mixture of para- and meta-cresol, can be practically any amount of para-cresol since practically any amount of para-cresol can be separated from the mixture as long the proper mole ratio of anhydrous inorganic salt to para-cresol is used. Generally, it is preferred that the para-cresol be present in the mixture of methylated and ethylated phenols in an amount of at least about 10 weight percent.

The anhydrous inorganic salts of calcium bromide, lithium bromide, manganese bromide or magnesium chloride that are used in the process of the present invention are the commercial anhydrous halide salts or the hydrated forms of the salts that have been dehydrated. Dehydration of the halide salts can be in any manner known to those skilled in the art. Anhydrous halide salts are readily prepared from hydrated forms such as aqueous solutions or flaked hydrate forms. It is preferred to heat either the aqueous or flaked form to around 200° C. in air to give the anhydrous material in a solid chunk, which may be then ball milled or ground for use.

In one embodiment of the present invention wherein complexation of para-cresol is accomplished firstly, a mixture of methylated and ethylated phenols that contains an amount of para-cresol and meta-cresol is treated to complex a substantial portion of the contained para-cresol by the use of one or more anhydrous inorganic halide salts (hereinafter referred to as salt). These halide salts are selected from calcium bromide, lithium bromide, manganese bromide or magnesium chloride. One or more of these halide salts is added to the mixture in an amount to give a mole ratio of the halide salt to the para-cresol in the mixture in the range of about 0.5 to one to about 1.5 to one. If the mole ratio of the salt to para-cresol is about 1.5 to one, other methylated or ethylated phenolic compounds may complex or may complex to an extent and complicate the separation of para-cresol from the mixture. If the mole ratio of halide salt to para-cresol is below 0.5 to one, then the maximum amount of para-cresol present in the mixture will not be separated and the yield of the process will be decreased. The preferred mole ratio of halide salt to para-cresol depends on the particular halide salt used. The preferred ranges of mole ratio of the halide salts to para-cresol are as follows: calcium bromide, about 0.8 to one to about 1.2 to one; lithium bromide, about 0.8 to one to about 1.2 to one; manganese bromide, about 0.8 to one to about 1.2 to one; and magnesium chloride, about 0.8 to one to about 1.2 to one. These ranges are all based on the mole ratio of halide salt to para-cresol contained in the mixture. To obtain the mole ratio of halide salt to para-cresol in the mixture, it is necessary to determine the amount of para-cresol in the mixture of the methylated and ethylated phenolic compounds. This can be done by any analytical technique known to those skilled in the art for determining the amount of para-cresol in a mixture of organic compounds.

The addition of the proper amount of halide salt can be performed in the presence or absence of a non-aqueous solvent. If the solvent is not present upon the initial addition of the halide salt to the mixture of methylated and ethylated phenolic compounds, it must be added at a later time when, upon formation of the complex, mixing of the halide salt and the components of the mixture becomes difficult. The non-aqueous solvent is added in an amount to facilitate mixing of the components. The non-aqueous solvent should not complex with the halide salt but, if complexing occurs, then the solvent must complex to a lesser extent than the para-cresol. A few examples of non-aqueous solvents that can be used are toluene, methylene chloride, chlorobenzene, ortho-dichlorobenzene, and lower aliphatic alicylic compounds such as hexane, as well as oxygenated compounds like ethers, ketones and esters, as long as any complex that is formed is weaker than the complex formed by the para-cresol. The preferred non-aqueous solvent is toluene because of its relatively low cost.

During the addition of the halide salt to the mixture and complexing of the halide salt and the para-cresol, the temperature is in the range of about ambient temperature, generally around 20° C., to about 130° C. at atmospheric pressure. If super-atmospheric or sub-atmospheric pressures are employed, the temperature will vary accordingly. Moderate increases in the temperature within this range during complexing will increase the rate of complex formation. If the complex is not initiated at the higher temperatures within the above range, the temperature can be lowered to initiate complexing and then raised to increase the rate of complexing. The higher temperatures are preferred when there is a small amount, e.g., around 15 weight percent, of the para-cresol in the mixture.

If complex formation with a particular halide salt is not initiated within a reasonable time, an initiator may be used to catalyze complex formation. Such initiators include normal-aliphatic alcohols such as anhydrous ethanol, anhydrous propanol and anhydrous butanol. A catalytically effective amount of alcohol to be used would be about 1 to about 10 weight percent. Another useful initiator is a previously formed para-cresol-salt complex. A complex of para-cresol and calcium bromide, or lithium bromide, or manganese bromide, or magnesium chloride, can be used to initiate complex formation. The catalytically effective amount of the complex used is again in the range of about 1 to about 10 weight percent of the mixture being treated. It is preferred that anhydrous ethanol be used as the complex initiator or, alternatively, a complex be used containing the same halide salt that is used to complex the para-cresol.

The time taken for the complex formation varies for the particular halide salt used. Lithium bromide is extremely fast in forming a complex with the para-cresol while calcium bromide, magnesium chloride and manganese bromide are somewhat slower. Lithium bromide forms a complex within about three to five minutes compared with several hours for the other halide salts. The preferred anhydrous halide salt that is used in the para-cresol complexing stage of the present invention is calcium bromide since it has high selectivity and provides good conversion.

Once the para-cresol-salt complex, preferably the para-cresol-calcium bromide complex, is formed, the complex is separated from the mixtures of methylated and ethylated phenols, preferably a mixture of para-cresol and meta-cresol. This separation can be by any method and in any equipment known to those skilled in the art for separation of a solid complex from a liquid solution. Preferably, the complex is separated by filtration to render a supernatant liquid containing the methylated and ethylated phenols including meta-cresol. The filtered complex of the para-cresol and the halide salt is decomposed to release the para-cresol and recover the halide salt that can be recycled for additional complexing.

In the second stage of this embodiment of the process of the present invention wherein complexation of the meta-isomer is accomplished subsequent to complexation of the para isomer, the supernatant liquid from the first stage that contains methylated and ethylated phenols and meta-cresol is treated with sodium acetate to complex the meta-cresol contained therein. It is an advantage of the process of this invention that a specific mole ratio or minimum amount of meta-cresol for complexation with sodium acetate is not required to accomplish efficient separation of the meta isomer. The sodium acetate is added to this mixture in a mole ratio typically in an amount in the range of about 1 to one to about 3 to one of sodium acetate to meta-cresol in the mixture. The addition and the complexing usually occur at a temperature in the range of about 0° C. to 75° C. Once the meta-cresol-sodium acetate complex is formed, the complex is separated from the mixture of methylated and ethylated phenols. This separation can be by any method and in any equipment known to those skilled in the art for separating a solid complex from a liquid solution. Preferably the complex is separated by filtration to produce a supernatant liquid that contains methylated and ethylated phenols that did not complex and uncomplexed meta-cresol and para-cresol. The meta-cresol obtained upon decomposition of the complex is a high purity meta-cresol that has a purity in the range of about 97–99 percent. When the mixture treated by the process of this invention is a mixture of para-cresol and meta-cresol, the supernatant liquid obtained after the meta-cresol complex is removed in the second stage also contains predominantly meta-cresol in a purity less than that obtained from the meta-cresol-sodium acetate complex. The purity of the meta-cresol in the supernatant liquid may typically be in the range of about 90–95 percent.

Before either the para-cresol-salt complex or the meta-cresol-sodium acetate complex is decomposed, it is preferred that the complexes be dried to remove the non-aqueous solvent. This drying may be done by any process known to those skilled in the art for drying a solid to remove a solvent. Preferably, the drying is performed by vaporizing the solvent at a temperature above the solvent's boiling point but less than the decomposition temperature for the complex. The recovered solvent obtained from the drying step can be recycled for use in either of the complexing steps.

In the decomposition of the para-cresol-salt complex and the meta-cresol-sodium acetate complex, decomposition of the two complexes is performed separately but in a similar fashion and thus will be discussed together. Decomposition is preferably performed by heating the para-cresol-salt complex to a decomposition temperature of about 200° C. at atmospheric pressure, and by hydrolyzing the meta-cresol-sodium acetate complex. Alternatively, the complexes can be decomposed by distilling the complex at a reduced pressure, or by hydrolysis in the case of the para-cresol-salt complex, or by cleavage with other agents such as an alcohol, that form stronger complexes than the para-cresol or meta-cresol complex. Thermal decomposition is preferred for releasing the para-cresol and meta-cresol isomers and recovering the halide salt and sodium acetate since it is the most economic method of decomposition and since the complexing agents recovered can be recycled for use in further complexing. The thermal decomposition can be performed in any equipment known to those skilled in the art useful in conducting decomposition reactions. Preferably, the thermal decomposition is performed in a Rinco evaporator at temperatures up to about 200° C. and under reduced pressure. Alternatively, the complexes can be decomposed at a temperature of around 125° C. under vacuum conditions. In another alternative embodiment, the para-cresol-salt complex can be hydrolyzed with a sufficient amount of water to decompose all of the complex. Also, since alcohols form a stronger complex than phenols, the alcohols can be used to cleave the complex such that the alcohol will be substituted in the complex for the para-cresol or the meta-cresol. The disadvantage of this decomposition method is that the solid complexing agent is not directly recoverable for recycling. When hydrolysis is used for decomposition, the halide salt or sodium acetate recovered would have to be dehydrated again before it could be recycled.

The para-cresol recovered from the decomposition reaction is much purer than the original mixture of methylated and ethylated phenolic compounds. The para-cresol may contain a minor amount of meta-cresol and other methylated and ethylated phenols such as ortho-ethylphenol. If improved purity is desired, the para-cresol can be complexed repeatedly similar to methods of fractional distillation. The meta-cresol recovered from the decomposition reaction is a high purity meta-cresol in the range of about 98+ percent purity, but may contain minor amounts of para-cresol and other methylated and ethylated phenols.

The complex formation of the para-cresol and the anhydrous inorganic halide salt and the complex formation of the meta-cresol-sodium acetate can be performed in conventional reaction equipment. Also, the complexing can be performed in a batch manner or a continuous manner where the reactants are cascaded from one reaction vessel to another.

DETAILED DESCRIPTION OF THE DRAWING

Figure 1:
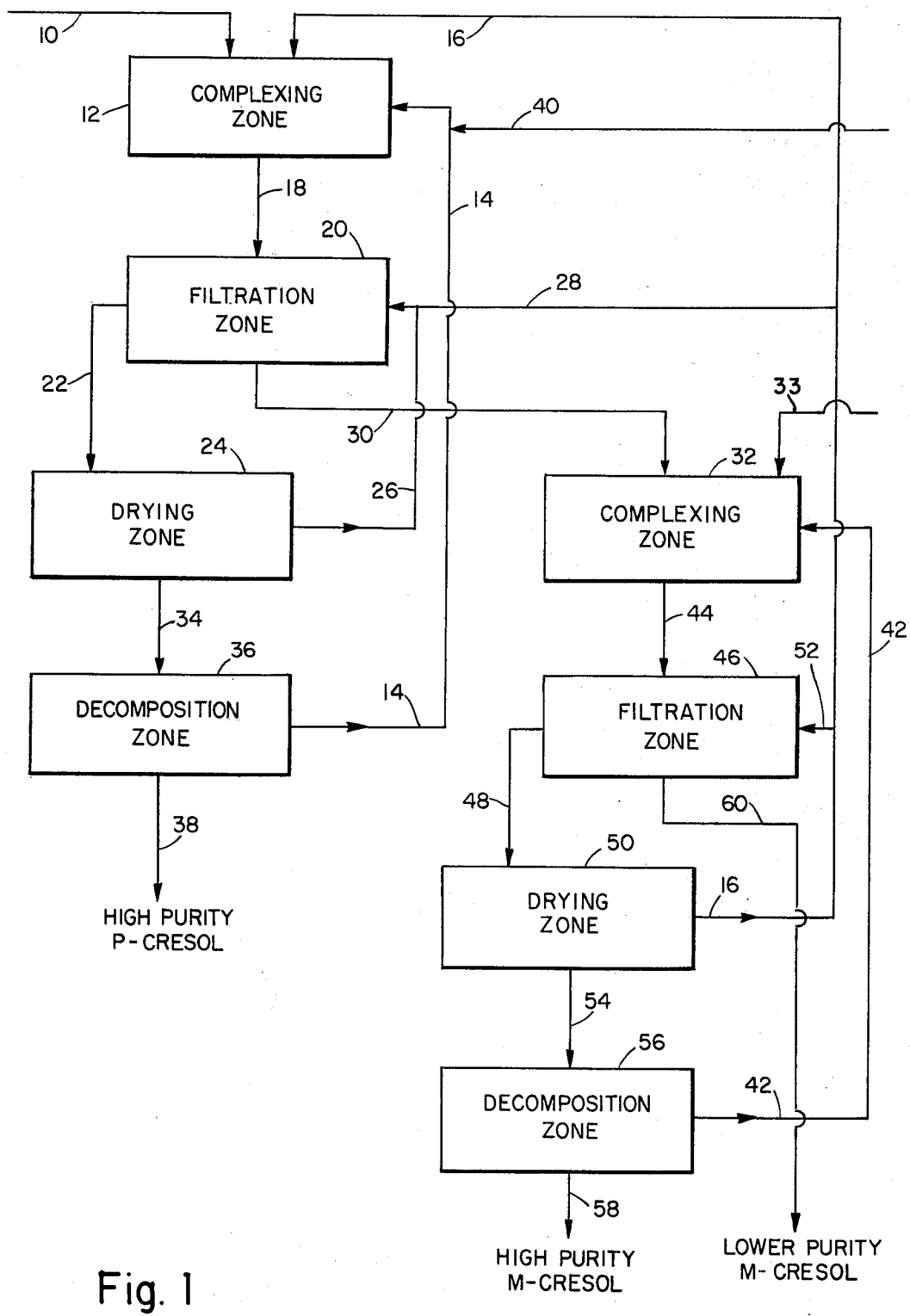
FIG. 1 is a flow diagram of a preferred embodiment of the present invention.

The mixture of methylated and ethylated phenols from which para-cresol and meta-cresol are separated in the preferred embodiment contains a two-to-one mole ratio of meta-cresol isomer to para-cresol isomer. This mixture enters a complexing zone 12 through a conduit 10 together with calcium bromide which enters the complexing zone through a conduit 14. The amount of calcium bromide added to complexing zone 12 is preferably an amount which will give a mole ratio of calcium bromide to para-cresol in the range of 0.7 to one to about 1.0 to one. A non-aqueous solvent, preferably toluene, is also added initially to complexing zone 12 through a conduit 16. In complexing zone 12, the mixture of meta- and para-cresol isomers, the toluene and the calcium bromide are mixed at a temperature of around 100° C. for about eight hours, there being sufficient toluene present to ensure thorough mixing of the components, during the complexation stage. At the end of this time a substantial portion of the para-cresol is complexed with calcium bromide and this complex, along with the supernatant liquid containing meta-cresol, is removed through a conduit 18 from complexing zone 12. The supernatant liquid may contain small quantities of ortho-cresol, xylenol, ortho-ethylphenol, or other methylated or ethylated phenols.

The supernatant liquid which includes the para-cresol complex leaves complexing zone 12 through conduit 18 and is conveyed into a filtration zone 20, where the complex is separated from the supernatant mixture. The wet para-cresol-calcium bromide complex is conveyed from filtration zone 20 through a conduit 22 to a drying zone 24, where the complex is dried and the toluene is separated from the complex. The toluene is then recycled through a conduit 26 to a conduit 28 where it is mixed with additional toluene and conveyed to filtration zone 20 to wash the wet complex. The supernatant liquid from which the para-cresol-calcium bromide complex has been removed is conveyed from filtration zone 20 via conduit 30 to complexing zone 32.

After the para-cresol-calcium bromide complex has been dried in zone 24, the complex is conveyed through a conduit 34 to decomposition zone 36. In zone 36 the complex is heated to a temperature of around 200° C. at atmospheric pressure to decompose the complex to produce para-cresol and to regenerate the calcium bromide salt. The product para-cresol product leaves decomposition zone 36 through conduit 38 and is of a purity of about 98 percent. The regenerated calcium bromide leaves decomposition zone 36 through conduit 14 and is conveyed to complexing zone 12 to further complex with the para-cresol isomer. In an alternative embodiment, additional calcium bromide can be added to conduit 14 through conduit 40 from an outside source (not shown).

After separation of the para-cresol isomer, the supernatant liquid typically has a concentration of the meta-cresol isomer of about 95 percent by weight of samples taken from the mixture. The supernatant liquid is delivered to complexing zone 32 through conduit 30 together with sodium acetate supplied through conduit 33. The supernatant liquid and the sodium acetate are mixed at a temperature in a range from about 20° C. to about 50° C. for four to ten hours to allow complexation of the meta-cresol isomer with the sodium acetate. The complex of meta-cresol-sodium acetate and the uncomplexed mixture is conveyed from complexing zone 32 through conduit 44 to filtration zone 46.

In filtration zone 46 the meta-cresol-sodium acetate complex is separated from the uncomplexed mixture. The complex is withdrawn from the filtration zone 46 through conduit 48 and delivered to drying zone 50. In drying zone 50 the complex is dried and toluene is removed through conduit 16. A portion of the toluene is introduced back into filtration zone 46 through conduit 52 to wash the wet meta-cresol-sodium acetate complex, with the remainder of the toluene returning through conduit 16 to complexing zone 12 for reuse in the complexing of para-cresol.

The dried complex is conveyed from drying zone 50 through conduit 54 to decomposition zone 56 wherein the meta-cresol-sodium acetate complex is decomposed by hydrolysis. The meta-cresol withdrawn from decomposition zone 56 through conduit 58 has a purity of around 98 percent. The regenerated sodium acetate withdrawn from decomposition zone 56 through conduit 42 is conveyed to complexing zone 32 for further complexing with the meta-cresol.

The uncomplexed mixture leaving filtration zone 46 by conduit 60 consists of 85–95 percent pure meta-cresol. This mixture can be used as a less pure meta-cresol product or can be treated in other ways to obtain pure meta-cresol.

The following examples set forth specific embodiments of the invention. However, the invention is not to be construed as being limited to these embodiments for there are, of course, numerous possible variations and modifications. All parts and percentages recited in the examples and throughout the specification are by weight, unless otherwise specified.

EXAMPLE I

A reaction vessel equipped with heating means, stirring means and drying means for removing water from the atmosphere in the reaction vessel is charged with 324 parts of a commercially available cresol isomer mixture comprising meta-cresol and para-cresol in a two-to-one molar ratio, 300 parts ball-milled anhydrous calcium bromide and about 800 parts toluene. The components are mixed and heated to about 100° C. for 11 hours. The solid complex is then filtered from the mixture, washed with toluene and hydrolyzed with water. Gas chromatographic analysis is made of the hydrolyzate and the filtrate solution. The hydrolyzate is found to comprise essentially all para-cresol, there being no meta-cresol isomer detected. The filtrate is found to have meta-cresol isomer and para-cresol isomer in a 96 to 4 molar ratio.

For experimental purposes, the 96/4 mixture of meta- and para-cresol is adjusted to a meta-/para-cresol ratio of 95/5. To a reaction vessel equipped as above, there is charged 120 parts of the 95/5 isomer mixture, together with 73.3 parts anhydrous sodium acetate, about 5 parts ethanol and about 660 parts hexane. The components are mixed at room temperature for about 18 hours. The solid complex is filtered from the mixture, washed with hexane, dried under reduced pressure and then hydrolyzed with water. Results of gas chromatographic analysis of the hydrolyzate and the filtrate are listed in Table I.

EXAMPLE II

To a reaction vessel equipped as in Example I, there is charged 120 parts of a 95/5 meta-cresol to para-cresol isomer mixture, together with 139 parts powdered anhydrous sodium acetate, about 5 parts ethanol and about 660 parts hexane. The components are mixed at room temperature for three hours. The solid complex is filtered from the mixture, washed with hexane, dried under reduced pressure and then hydrolyzed with water. Results of gas chromatographic analysis of the hydrolyzate and the filtrate are listed in Table I.

EXAMPLE III

A reaction vessel equipped as in Example I is charged with 60 parts of a 95/5 meta-cresol to para-cresol isomer mixture, 139 parts anhydrous sodium acetate, about 5 parts ethanol and about 660 parts hexane. The mixture is treated generally in accordance with the procedures outlined in Example II, except that mixing of the components proceeds for about 16 hours. Data from the analysis of the hydrolyzate and filtrate are listed in Table I.

EXAMPLE IV

A reaction vessel equipped as in Example I is charged with 60 parts of a 95/5 meta-cresol to para-cresol isomer mixture, 278 parts anhydrous sodium acetate, about 5 parts ethanol and about 660 parts hexane. The mixture is treated generally in accordance with the procedures outlined in Example II, except that mixing of the components proceeds for about 18 hours. Data from the analyses of the hydrolyzate and filtrate are listed in Table I.

EXAMPLE V

A reaction vessel equipped as in Example I is charged with 60 parts of a mixture having meta-cresol and para-cresol in a two-to-one molar ratio, 139 parts anhydrous sodium acetate, about 5 parts ethanol and about 660 parts hexane. The mixture is treated generally in accordance with the procedures of Example II, except that mixing of the components proceeds for about 24 hours. Data from the analyses of the hydrolyzate and filtrate are listed in Table I.

TABLE I

| Example | Component | Second Stage Separation Ratio of m-cresol to p-cresol |
|---|---|---|
| I | Hydrolyzate | 99.97/0.03 |
|  | Filtrate | 92.72/7.28 |
| II | Hydrolyzate | 99.96/0.04 |
|  | Filtrate | 85.42/14.58 |
| III | Hydrolyzate | 99.98/0.02 |
|  | Filtrate | 76.52/23.48 |
| IV | Hydrolyzate | 100.0/0.0 |
|  | Filtrate | 76.56/23.44 |
| V | Hydrolyzate | 99.23/0.77 |
|  | Filtrate | 47.57/52.43 |

Although specific examples of the instant invention have been set forth hereinabove, it is not intended that the invention be limited solely thereto, but is to include all the variations and modifications falling within the scope of the appended claims.

I claim:

1. A process for separating para-cresol and metacresol isomers from a mixture comprising methylated and ethylated phenols, the process comprising the steps of:
    (a) for separation of the para-cresol isomer, adding to the mixture comprising methylated and ethylated phenols one or more anhydrous or dehydrated inorganic halide salts selected from the group consisting of calcium bromide, lithium bromide, manganese bromide and magnesium chloride, in an amount to give a mole ratio of said one or more salts to para-cresol in the mixture in a range of about 0.5 to one to about 1.5 to one, so as to produce a complex between predominantly para-cresol and the halide salt, the mixture having a temperature in a range from about 20° C. to about 130° C. during the halide salt adding step,
    whereby the para-cresol-salt complex may be separated from the mixture comprising methylated and ethylated phenols, and then decomposed to produce predominantly para-cresol; and
    (b) for separation of the meta-cresol isomer, adding to the mixture comprising methylated and ethylated phenols from which para-cresol has been removed an amount of sodium acetate to give a mole ratio of said sodium acetate to meta-cresol in the mixture in a range of 0.5 to one to about 5 to one, so as to produce meta-cresol-sodium acetate complex, the mixture having a temperature in a range from about 0° C. to about 75° C. during the sodium acetate adding step,
    whereby the meta-cresol-sodium acetate complex may be separated from the mixture comprising methylated and ethylated phenols from which para-cresol has been removed, and then decomposed to produce predominantly meta-cresol.

2. The process of claim 1 wherein the anhydrous salt is added to the mixture in the presence of a non-aqueous solvent.

3. The process of claim 1 wherein the sodium acetate is added to the mixture in the presence of a non-aqueous solvent.

4. The process of claim 2 or 3 wherein the non-aqueous solvent is toluene.

5. The process of claim 1 wherein the anhydrous or dehydrated inorganic halide salt is para-activated calcium bromide.

6. The process of claim 1 wherein the sodium acetate used to complex with the meta-cresol isomer is meta-activated sodium acetate.

7. The process of claim 1 wherein the mixture from which para-cresol has been removed is a meta-cresol-rich mixture having at least 2 to 1 mole ratio of meta-cresol to any other methylated and ethylated phenol.

8. The process of claim 1 further comprising the steps of:
    separating said para-cresol-salt complex and said meta-cresol-sodium acetate complex from their respective mixtures; and
    decomposing said para-cresol-salt complex and said meta-cresol-sodium acetate complex to produce, respectively, para-cresol and meta-cresol.

9. The process of claim 8 further comprising drying the para-cresol-containing complex or the meta-cresol-containing complex, or both, after separation of the complex from the mixture and before the complexes are decomposed.

10. The process of claim 9 wherein non-aqueous solvent obtained from drying is recycled to the complexing step.

11. The process of claim 8 wherein the para-cresol-salt complex is decomposed by thermal decomposition at atmospheric pressure.

12. The process of claim 8 wherein the meta-cresol-sodium acetate complex is decomposed by hydrolysis with water or alcohol.

13. The process of claim 8 wherein one or both of the complexes are decomposed by treatment with alcohol by cleavage with a lower aliphatic alcohol.

14. The process of claim 8 wherein the inorganic halide salt obtained from decomposing the para-cresol-salt complex is recycled for further complexing of para-cresol.

15. The process of claim 8 wherein the sodium acetate obtained from decomposition of the meta-cresol-sodium acetate complex is recycled for further complexing of meta-cresol.

16. The process of claim 8 wherein one or both of the complexes are decomposed by distillation at reduced pressure.

17. A process for separating para-cresol and meta-cresol isomers from a mixture comprising methylated and ethylated phenols, the process comprising the steps of:
    (a) for separation of the meta-cresol isomer, adding to the mixture comprising methylated and ethylated phenols an amount of sodium acetate to give a mole ratio of said sodium acetate to meta-cresol in the mixture in a range of about 0.5 to one to about 5 to one, so as to produce meta-cresol-sodium acetate complex, the mixture having a temperature in a range from about 0° C. to about 75° C. during the sodium acetate adding step, whereby the meta-cresol-sodium acetate complex may be separated from the mixture comprising methylated and ethylated phenols, and then decomposed; to produce predominantly meta-cresol and (b) for separation of the para-cresol isomer, adding to the mixture comprising methylated and ethylated phenols from which meta-cresol has been removed one or more anhydrous or dehydrated inorganic halide salts selected from the group consisting of calcium bromide, lithium bromide, manganese bromide and magnesium chloride, in an amount to give a mole ratio of said one or more salts to para-cresol in the mixture in a range of about 0.5 to one to about 1.5 to one, so as to produce a complex between predominantly para-cresol and the halide salt, the mixture having a temperature in a range from about 20° C. to about 130° C. during the halide salt adding step, whereby the para-cresol-salt complex may be separated from the mixture comprising methylated and ethylated phenols from which meta-cresol has been removed, and then decomposed to produce predominantly para-cresol.

18. The process of claim 17 wherein the anhydrous or dehydrated inorganic salt is para-activated calcium bromide.

19. The process of claim 17 further comprising the steps of:
separating said meta-cresol-sodium acetate complex and said para-cresol-salt complex from their respective mixtures; and
decomposing said meta-cresol-sodium acetate complex and said para-cresol-salt complex to produce, respectively, meta-cresol and para-cresol.

20. The process of claim 19 further comprising drying the meta-cresol-containing complex or the para-cresol-containing complex, or both, after separation of the complexes from the mixture and before the complexes are decomposed.

21. The process of claim 20 wherein non-aqueous solvent obtained from drying is recycled to the complexing step.

22. The process of claim 19 wherein the para-cresol-salt complex is decomposed by thermal decomposition at atmospheric pressure.

23. The process of claim 19 wherein the meta-cresol-sodium acetate complex is decomposed by hydrolysis with water or alcohol.

24. The process of claim 19 wherein one or both of the complexes are decomposed by treatment with alcohol by cleavage with a lower aliphatic alcohol.

25. The process of claim 19 wherein the inorganic salt obtained from decomposing the para-cresol-salt complex is recycled for further complexing of para-cresol.

26. The process of claim 19 wherein the sodium acetate obtained from decomposition of the meta-cresol-sodium acetate complex is recycled for further complexing of meta-cresol.

27. The process of claim 17 wherein the sodium acetate is added to the mixture in the presence of a non-aqueous solvent.

28. The process of claim 17 wherein the halide salt is added to the mixture in the presence of a non-aqueous solvent.

29. The process of claim 19 wherein one or both of the complexes are decomposed by distillation at reduced pressure.

* * * * *